United States Patent
Hirata et al.

(10) Patent No.: US 10,677,704 B2
(45) Date of Patent: Jun. 9, 2020

(54) SYSTEM FOR ANALYZING CARBON DIOXIDE CONCENTRATION OF AMINE-BASED ABSORBING SOLUTION, CARBON DIOXIDE RECOVERY SYSTEM, AND METHOD OF OPERATING THE SAME

(71) Applicant: Mitsubishi Heavy Industries Engineering, Ltd., Kanagawa (JP)

(72) Inventors: Takuya Hirata, Tokyo (JP); Masakazu Sakaguchi, Tokyo (JP); Tatsuya Tsujiuchi, Tokyo (JP); Hiroshi Tanaka, Tokyo (JP)

(73) Assignee: Mitsubishi Heavy Industries Engineering, Ltd., Kanagawa (JP)

( * ) Notice: Subject to any disclaimer, the term of this patent is extended or adjusted under 35 U.S.C. 154(b) by 264 days.

(21) Appl. No.: 15/773,837

(22) PCT Filed: Oct. 26, 2016

(86) PCT No.: PCT/JP2016/081690
§ 371 (c)(1),
(2) Date: May 4, 2018

(87) PCT Pub. No.: WO2017/077914
PCT Pub. Date: May 11, 2017

(65) Prior Publication Data
US 2018/0321122 A1 Nov. 8, 2018

(30) Foreign Application Priority Data
Nov. 5, 2015 (JP) .................................. 2015-217689

(51) Int. Cl.
*B01D 53/14* (2006.01)
*G01N 11/00* (2006.01)
(Continued)

(52) U.S. Cl.
CPC ......... *G01N 11/00* (2013.01); *B01D 53/1412* (2013.01); *B01D 53/1418* (2013.01);
(Continued)

(58) Field of Classification Search
CPC ........ B01D 2252/204; B01D 2257/504; B01D 53/1412; B01D 53/1418; B01D 53/1425;
(Continued)

(56) References Cited

U.S. PATENT DOCUMENTS

| 6,350,426 B1 * | 2/2002 | Sota .................... G01N 29/024 423/483 |
| 2012/0167760 A1 | 7/2012 | Muraoka et al. |
| 2014/0241967 A1 | 8/2014 | Fujita et al. |

FOREIGN PATENT DOCUMENTS

| EP | 990898 A1 | 4/2000 |
| JP | 3564575 B2 | 9/2004 |

(Continued)

OTHER PUBLICATIONS

Supplementary European Search Report in corresponding European Application No. 16861976.5, dated Jun. 24, 2019 (7 pages).

*Primary Examiner* — Cabrena Holecek
(74) *Attorney, Agent, or Firm* — Osha Liang LLP

(57) ABSTRACT

A system for analyzing a $CO_2$ concentration of an amine-based absorbing solution includes a measurement apparatus that measures a viscosity of the amine-based absorbing solution and at least one selected from conductivity and ultrasonic propagation velocity of the amine-based absorbing solution, wherein the amine-based absorbing solution absorbs and removes $CO_2$ from a target gas by gas-liquid contact with the target gas; and a controller that determines the $CO_2$ concentration of the amine-based absorbing solution from results measured by the measurement apparatus.

8 Claims, 9 Drawing Sheets

(51) Int. Cl.
    *G01N 33/00*     (2006.01)
    *G01N 29/024*     (2006.01)

(52) U.S. Cl.
    CPC ..... *B01D 53/1425* (2013.01); *B01D 53/1475* (2013.01); *G01N 29/024* (2013.01); *G01N 33/00* (2013.01); *B01D 2252/204* (2013.01); *B01D 2257/504* (2013.01); *Y02A 50/2342* (2018.01); *Y02C 10/04* (2013.01); *Y02C 10/06* (2013.01)

(58) Field of Classification Search
    CPC .. B01D 53/1475; G01N 11/00; G01N 29/024; G01N 33/00; Y02A 50/2342; Y02C 10/04; Y02C 10/06
    See application file for complete search history.

(56) References Cited

FOREIGN PATENT DOCUMENTS

| | | |
|---|---|---|
| JP | 2006-184258 A | 7/2006 |
| JP | 2012-152731 A | 8/2012 |
| WO | 2013/81126 A1 | 6/2013 |

\* cited by examiner

SYSTEM FOR ANALYZING CARBON DIOXIDE CONCENTRATION OF AMINE-BASED ABSORBING SOLUTION, CARBON DIOXIDE RECOVERY SYSTEM, AND METHOD OF OPERATING THE SAME

TECHNICAL FIELD

One or more embodiments of the present invention relate to a system for analyzing the concentration of carbon dioxide ($CO_2$) in an amine-based absorbing solution, a $CO_2$ recovery system, and a method of operating the same.

BACKGROUND

Various methods have been proposed for removing and recovering acid gases, such as $CO_2$ and $H_2S$, contained in exhaust gases from fossil fuel combustion. In one of such methods, an amine-based absorbing solution such as an alkanolamine aqueous solution is brought into contact with combustion exhaust gas to absorb $CO_2$ from the combustion exhaust gas. This amine-based absorbing solution having absorbed $CO_2$ is heated to release $CO_2$, thereby recovering $CO_2$ and regenerating the amine-based absorbing solution for cyclic use.

In such a $CO_2$ recovery system, it is necessary to determine optimal operation conditions from the viewpoints of ensuring the required gas absorption performance and reducing the necessary energy. It is therefore important to measure and know the amine concentration in the absorbing solution and the $CO_2$ concentration in the absorbing solution during operation of the system. Patent Document 1 states that since the $CO_2$ concentration in the amine-based absorbing solution correlates with the ultrasonic propagation velocity and electric conductivity of the amine-based absorbing solution, the ultrasonic propagation velocity or electric conductivity is measured, and the operation conditions are controlled by using the $CO_2$ concentration in the amine-based absorbing solution calculated from the measured value.

Patent Document 2, which does not relate to the aforementioned $CO_2$ recovery system, describes a technique capable of determining the concentration of each of plural (n) solutes dissolved in a solvent by measuring the ultrasonic propagation velocity in the solvent and by detecting n−1 types of specific properties for each solute. Patent Document 3 describes calculation of the concentration of each component of a three-component mixture composed of sulfuric acid, hydrogen fluoride, and water by measuring the ultrasonic propagation velocity and one of the electric conductivity and viscosity in the mixture.

REFERENCE DOCUMENT LIST

Patent Documents

Patent Document 1: JP 2012-152731 A
Patent Document 2: JP 2006-184258 A
Patent Document 3: JP 3564575 B Since a boiler that produces combustion exhaust gas as the target gas frequently fluctuates in operating status, the aforementioned $CO_2$ recovery system needs to change the operation conditions according to the aforementioned operating status. Accordingly, there is a demand for online measurement and monitoring of the $CO_2$ concentration of the amine-based absorbing solution. However, the $CO_2$ concentration of the amine-based absorbing solution has not previously been directly measured, but is currently being measured by sampling the amine-based absorbing solution and analyzing the samples with a precision instrument.

Patent Document 1 describes a technique to automatically take measurements of the amine-based absorbing solution flowing in the system online. However, even if the ultrasonic propagation velocity and electric conductivity of the amine-based absorbing solution are measured, the $CO_2$ concentration in the amine-based absorbing solution cannot always be specified because the measured ultrasonic propagation velocity or electric conductivity and the $CO_2$ concentration to be calculated do not have a one-to-one correlation in some cases depending on the amine concentration in the amine-based absorbing solution.

SUMMARY

One or more embodiments of the present invention provide a system for analyzing the $CO_2$ concentration of the amine-based absorbing solution, a $CO_2$ recovery system, and a method of operating the same, which are capable of automatically measuring the $CO_2$ concentration of the amine-based absorbing solution online regardless of whether the amine concentration in the amine-based absorbing solution is high or low.

One or more embodiments of the present invention provide a system for analyzing a $CO_2$ concentration of an amine-based absorbing solution, the system including: a measurement apparatus for measuring viscosity and at least one selected from conductivity and ultrasonic propagation velocity of the amine-based absorbing solution, the amine-based absorbing solution being capable of absorbing and removing $CO_2$ from target gas containing at least $CO_2$ by gas-liquid contact with the target gas; and a controller for determining at least $CO_2$ concentration of the amine-based absorbing solution from results measured by the measurement apparatus.

The controller may determine the $CO_2$ concentration of the amine-based absorbing solution by correcting a measured conductivity of the amine-based absorbing solution by use of a measured viscosity thereof based on a correlation between corrected values of conductivities of the amine-based absorbing solution using viscosities thereof and $CO_2$ concentrations of the amine-based absorbing solution.

The controller may determine the $CO_2$ concentration and amine concentration of the amine-based absorbing solution from a measured viscosity and a measured conductivity or ultrasonic propagation velocity of the amine-based absorbing solution based on a correlation among viscosities of the amine-based absorbing solution, conductivities or ultrasonic propagation velocities of the amine-based absorbing solution, $CO_2$ concentrations and amine concentrations of the amine-based absorbing solution.

The controller may determine the $CO_2$ concentration and amine concentration of the amine-based absorbing solution from three measured values of ultrasonic propagation velocity, viscosity, and conductivity of the amine-based absorbing solution based on a correlation among corrected values of ultrasonic propagation velocities of the amine-based absorbing solution using viscosities thereof, conductivities or corrected values of conductivities of the amine-based absorbing solution using viscosities thereof, $CO_2$ concentrations and amine concentrations of the amine-based absorbing solution.

The measurement apparatus may be capable of measuring a temperature of the amine-based absorbing solution, and the controller may determine the $CO_2$ concentration of the amine-based absorbing solution or the $CO_2$ concentration and amine concentrations of the amine-based absorbing solution from a measured viscosity of the amine-based absorbing solution, at least one selected from a measured conductivity and a measured ultrasonic propagation velocity of the amine-based absorbing solution, and a measured temperature of the amine-based absorbing solution.

The measurement apparatus may be capable of measuring viscosity and at least one selected from conductivity and ultrasonic propagation velocity of the amine-based absorbing solution at a certain temperature after the $CO_2$ absorbing solution is adjusted to the certain temperature.

Another aspect of the present invention is a $CO_2$ recovery system, including: a $CO_2$ absorption tower for removing $CO_2$ from target gas containing at least $CO_2$ by gas-liquid contact of an amine-based absorbing solution with the target gas to cause the amine-based absorbing solution to absorb $CO_2$; an absorbing solution regeneration tower for releasing $CO_2$ from the amine-based absorbing solution having absorbed $CO_2$ in the $CO_2$ absorption tower to regenerate the amine-based absorbing solution; and the aforementioned system for analyzing a $CO_2$ concentration of the amine-based absorbing solution.

One or more embodiments of the present invention provide a method of operating the aforementioned $CO_2$ recovery system, the method including: measuring viscosity of the amine-based absorbing solution and at least one selected from conductivity and ultrasonic propagation velocity of the amine-based absorbing solution; and determining at least $CO_2$ concentration of the amine-based absorbing solution from results comprising a measured viscosity and at least one selected from a measured conductivity and a measured ultrasonic propagation velocity of the amine-based absorbing solution.

As described above, according to one or more embodiments of the present invention, the viscosity of the amine-based absorbing solution and at least one selected from the conductivity and ultrasonic propagation velocity thereof, which may be automatically measured online, are measured. This allows for highly-accurate and quick calculation of the $CO_2$ concentration of the amine-based absorbing solution using a measured value of the viscosity regardless of whether the amine concentration of the amine-based absorbing solution is high or low since the value of the conductivity corrected using the viscosity correlates with the $CO_2$ concentration of the amine-based absorbing solution; the viscosity of the amine-based absorbing solution, the conductivity or ultrasonic propagation velocity of the amine-based absorbing solution, and the $CO_2$ concentration correlate with each other; or the value of the ultrasonic propagation velocity of the amine-based absorbing solution corrected using the viscosity, the conductivity or the value of the conductivity corrected using the viscosity, and the $CO_2$ concentration of the amine-based absorbing solution correlate with each other.

Moreover, the viscosity, conductivity, and ultrasonic propagation velocity of the amine-based absorbing solution depend on the temperature of the amine-based absorbing solution. Thus, the $CO_2$ concentration of the amine-based absorbing solution can be calculated quickly with high accuracy by controlling the temperature of the amine-based absorbing solution where the above-mentioned properties are to be measured, or by additionally measuring the temperature of the amine-based absorbing solution and correcting the measured values of the above-mentioned properties according to the measured value of the temperature, if necessary.

DETAILED DESCRIPTION OF THE EMBODIMENTS

Hereinafter, a system for analyzing a $CO_2$ concentration of an amine-based absorbing solution, a $CO_2$ recovery system, and a method of operating the same according to one or more embodiments of the present invention will now be described in detail with reference to the accompanying drawings.

Figure 1:
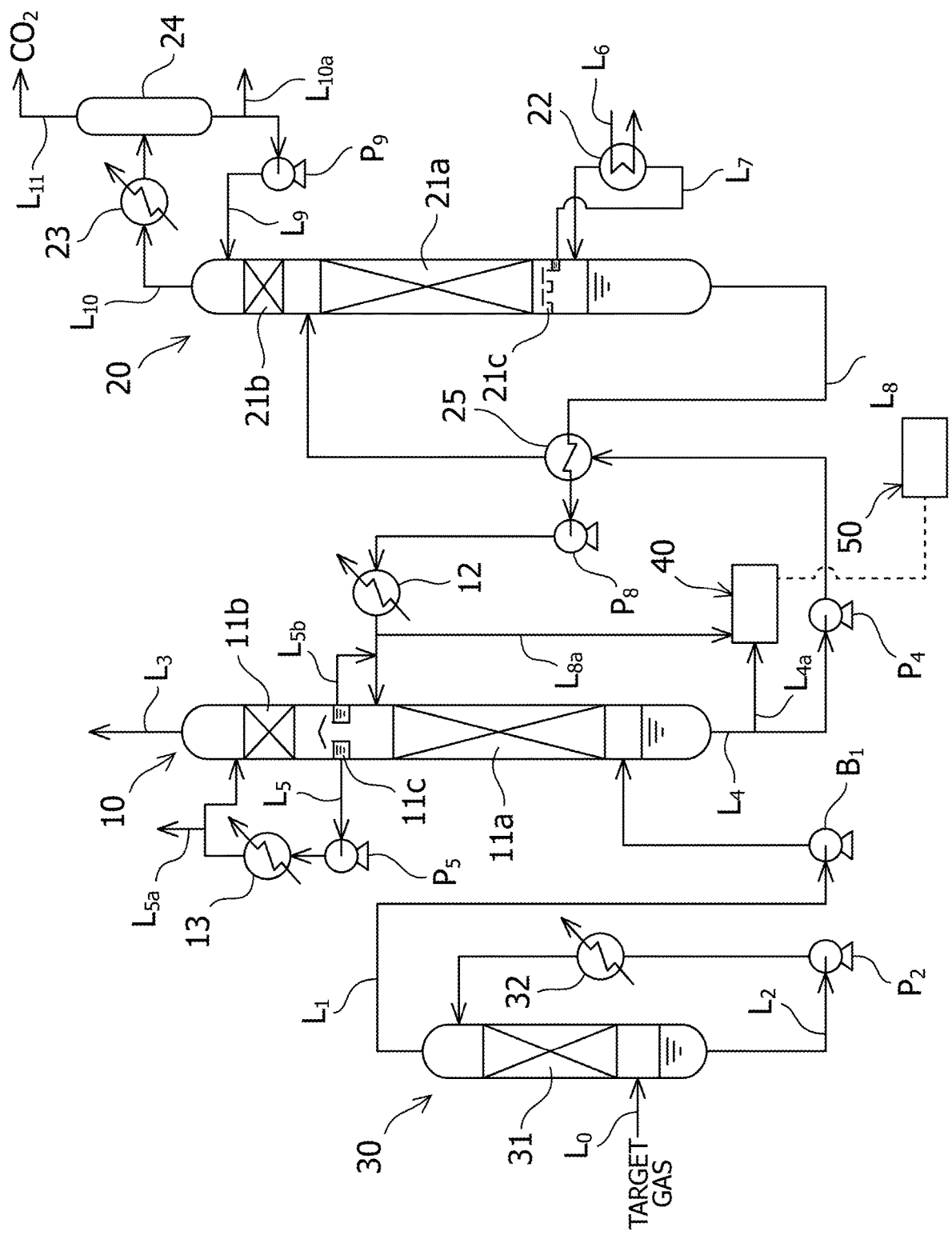
FIG. 1 is a schematic diagram showing a $CO_2$ recovery system according to one or more embodiments of the present invention.

As illustrated in FIG. 1, the $CO_2$ recovery system of one or more embodiments of the present invention include at least an absorption tower 10, a regeneration tower 20, and a measurement apparatus 40. The absorption tower 10 removes $CO_2$ from target gas containing $CO_2$ by bringing the $CO_2$-contained target gas into gas-liquid contact with an amine-based absorbing solution to cause the amine-based absorbing solution to absorb $CO_2$. The regeneration tower 20 causes the amine-based absorbing solution having absorbed $CO_2$ (rich solution) to release $CO_2$ for regenerating the amine-based absorbing solution having released $CO_2$ (lean solution) as the $CO_2$ absorbing solution. The measurement apparatus 40 measures the conductivity and viscosity of the amine-based absorbing solution. When the target gas contains acid gases such as $H_2S$ in addition to $CO_2$, such acid gases are also absorbed by the amine-based absorbing solution, which is not particularly described in this specification. FIG. 1 is a diagram for explaining the gist of one or more embodiments of the present invention and does not show some of attached devices.

The absorption tower 10 is provided with: a line $L_1$ in the lower part thereof to supply the target gas containing $CO_2$ into the absorption tower 10; and a line $L_3$ in the top to discharge the target gas having the acid gas removed, out of the absorption tower 10. The absorption tower 10 includes a lower packed section 11a and an upper packed section 11b between the position where the absorption tower 10 is connected to the line $L_1$ and the position where the absorption tower 10 is connected to the line $L_3$. In the lower packed section 11a, the target gas comes into gas-liquid contact with the amine-based absorbing solution. In the upper packed section 11b, the target gas having come into contact with the amine-based absorbing solution comes into gas-liquid contact with a cleaning solution. The absorption tower 10 further includes a water receiver 11c located between the upper and lower packed sections 11b and 11a. The water receiver 11c allows upward passage of gas but does not allow downward passage of liquid. The water receiver 11c is provided with a line $L_5$ that supplies liquid collected in the water receiver 11c, as a cleaning solution, into the absorption tower 10 above the upper packed section 11b. This line $L_5$ is provided with a pump $P_5$ that feeds the cleaning solution, a cooler 13 that cools the cleaning solution, and a line $L_{5a}$ that samples some of the cleaning solution and feeds the same to the measurement apparatus 40.

In the bottom of the absorption tower 10, a line $L_4$ is provided. The line $L_4$ feeds some of the amine-based absorbing solution having absorbed $CO_2$ (rich solution) to the regeneration tower 20. The line $L_4$ is provided with a line $L_{4a}$, a pump $P_4$, and a heat exchanger 25, which are sequentially arranged from the absorption tower 10 side. The line $L_{4a}$ samples some of the amine-based absorbing solution and feeds the same to the measurement apparatus 40. The pump $P_4$ feeds the amine-based absorbing solution. The heat exchanger 25 exchanges heat between the rich solution and the later-described lean solution.

The regeneration tower 20 includes a lower packed section 21a under the position of the line $L_4$ where the rich solution is supplied and an upper packed section 21b. The lower packed section 21a causes the rich solution to release $CO_2$. The upper packed section 21b washes the released $CO_2$ gas with reflux water described later. The regeneration tower 20 includes an absorbing solution receiver 21c under the lower packed section 21a. The absorbing solution receiver 21c is configured to allow upward passage of gas and not allow downward passage of liquid. The absorbing solution receiver 21c is provided with a line $L_7$ that supplies the rich solution collected in the absorbing solution receiver 21c into the regeneration tower 20 under the absorbing solution receiver 21c. The line $L_7$ is provided with a reboiler 22. The reboiler 22 heats the rich solution to release $CO_2$ from the rich solution. The reboiler 22 is provided with a line $L_6$ that supplies saturated steam for heating to the reboiler 22.

In the top of the regeneration tower 20, a line $L_{10}$ is provided, that discharges $CO_2$ gas released from the rich solution, out of the regeneration tower 20. The line $L_{10}$ is provided with a cooler 23 that cools the $CO_2$ gas and a gas-liquid separator 24 that separates condensed water generated by cooling from the $CO_2$ gas. The gas-liquid separator 24 is provided with a line $L_9$ that supplies the separated condensed water to above the upper packed section 21b in the regeneration tower 20 as reflux water and a line $L_{11}$ that discharges the separated $CO_2$ gas out of the system. The line $L_9$ for reflux water is provided with a line $L_{10a}$ that samples some of the amine-based absorbing solution and feeds the same to the measurement apparatus 40 and a pump $P_9$ that feeds the reflux water.

In the bottom of the regeneration tower 20, a line $L_8$ is provided. The line $L_8$ supplies the lean solution which is heated and regenerated by the reboiler 22 to above the lower packed section 11a in the absorption tower 10. This line $L_8$ is provided with the heat exchanger 25, a pump $P_8$, a cooler 12, a line $L_{8a}$, and a line $L_{5b}$, which are sequentially arranged from the regeneration tower 20 side. The heat exchanger 25 exchanges heat between the lean solution and the rich solution flowing through the line $L_4$. The pump $P_8$ feeds the lean solution. The cooler 12 cools the lean solution. The line $L_{8a}$ samples some of the amine-based absorbing solution and feeds the same to the measurement apparatus 40. The line $L_{5b}$ adds some of the cleaning solution collected in the water receiver 11c of the absorption tower 10 to the lean solution as makeup water.

In the upstream side of the absorption tower 10 in the flow direction of the target gas, a cooling tower 30 is provided. The cooling tower 30 cools the target gas before the target gas is supplied to the absorption tower 10. The cooling tower 30 is provided with a line $L_0$ in the lower part and the line $L_1$ in the top. The line $L_0$ supplies the target gas into the cooling tower 30. The line $L_1$ discharges the cooled target gas from the cooling tower 30 and supplies the same to the absorption tower 10. The cooling tower 30 includes a packed section 31 between the position where the cooling tower 30 is connected to the line $L_0$ and the position where the cooling tower 30 is connected to the line $L_1$. The packed section 31 is configured to bring cooling water and the target gas into contact with each other. The line $L_1$, which supplies the target gas, is provided with a blower $B_1$ for feeding the target gas. In the bottom of the cooling tower 30, a line $L_2$ is provided, that supplies cooling water collected in the bottom to above the packed section 31 in the cooling tower 30. The line $L_2$ is provided with a cooler 32 to cool the cooling water.

The measurement apparatus 40 is not particularly limited as long as the measurement apparatus 40 is capable of measuring the conductivity and viscosity of the amine-based absorbing solution. The measurement apparatus 40 may be an apparatus including a publicly known conductivity meter and viscometer. The measurement apparatus 40 is illustrated as a single unit in FIG. 1 but may be composed of two different apparatuses. The measurement apparatus 40 is also capable of measuring the temperature of the amine-based absorbing solution.

FIG. 1 illustrates the lines $L_{4a}$ and $L_{8a}$, which supply some of the amine-based absorbing solution to the measurement apparatus 40 for measurement of the conductivity and viscosity. The present invention is not limited thereto. A sensor to measure the conductivity and a sensor to measure the viscosity may be provided within the lines $L_4$ and $L_8$ for the amine-based absorbing solution between the absorption tower 10 and the regeneration tower 20, respectively. FIG. 1 illustrates the two lines $L_{4a}$ and $L_{8a}$ as supply lines to the measurement apparatus 40 for measurement of the conductivity and viscosity of both the rich solution and lean solution of the amine-based absorbing solution. The present invention is not limited thereto. The system may be configured to measure the conductivity and viscosity of one of the rich solution and lean solution of the amine-based absorbing solution.

In FIG. 1, the rich solution is sampled for measurement by the measurement apparatus 40 or is measured on the absorption tower 10 outlet side in the line $L_4$ for the rich solution where the temperature of the amine-based absorbing solution is comparatively stable. The present invention is not limited thereto. The rich solution may be sampled or measured on the regenerator tower 20 inlet side in the line $L_4$ or both on the absorption tower 10 outlet side and regeneration tower 20 inlet side. In FIG. 1, the lean solution is sampled for measurement by the measurement apparatus 40 or is measured on the absorption tower 10 inlet side in the line $L_8$ for the lean solution where the temperature of the amine-based absorbing solution is stable due to the cooler 12 and the like. The present invention is not limited thereto. The lean solution may be sampled or measured on the regenerator tower 20 outlet side in the line $L_8$ or both on the absorption tower 10 inlet side and regeneration tower 20 outlet side. If necessary, a temperature adjuster may be provided to cool or heat the rich and lean solutions to be measured by the measurement apparatus 40. This can keep constant the temperature of the amine-based absorbing solution to be measured by the measurement apparatus 40.

The measurement apparatus 40, which is configured to measure the conductivity and viscosity of the amine-based absorbing solution, is capable of measuring the conductivity and viscosity of the cleaning solution cyclically used in the upper packed section 11b of the absorption tower 10 and the reflux water cyclically used in the upper packed section 21b of the regeneration tower 20. FIG. 1 illustrates the lines $L_{5a}$ and $L_{10a}$, which supply some of the cleaning solution and reflux water to the measurement apparatus 40. However, sensors to measure the conductivity and viscosity may be provided within the lines $L_5$ and $L_{10}$ as described above.

The measurement apparatus 40 is configured to communicate with the controller 50. Results of measurements are transmitted to the controller 50 online.

The controller 50 includes a function to calculate the $CO_2$ concentration of the amine-based absorbing solution from the measured values of the conductivity and viscosity obtained by the measurement apparatus 40 based on the correlation between the value of the conductivity of the amine-based absorbing solution corrected using the viscosity and the $CO_2$ concentration of the amine-based absorbing solution. The value of the conductivity of the amine-based absorbing solution corrected using the viscosity can be the product of the conductivity and the viscosity of the amine-based absorbing solution, the product of the conductivity of the amine-based absorbing solution and an exponential function with a base of the viscosity, and the like, for example. The controller 50 includes a function to transmit a signal to change operation conditions (the flow rate of the amine-based absorbing solution, the amount of heat supplied to the reboiler 22, the flow rate of the target gas, and the like) of the $CO_2$ recovery system based on the calculated values of the $CO_2$ concentration. In one or more embodiments, the range of the $CO_2$ concentration in the aforementioned correlation is preferably 0.5 to 20 wt % and more preferably 1 to 15 wt %. In one or more embodiments, the range of the amine concentration is preferably 20 to 70 wt % and more preferably 40 to 60 wt %.

Next, the operation of the thus-configured system is described for explanation of the method of operating the $CO_2$ recovery system according to one or more embodiments of the present invention.

First, the target gas containing $CO_2$ is supplied from the line $L_0$ to the cooling tower 30 to be cooled. The target gas is gas containing at least $CO_2$, including natural gas, process gas produced at a chemical plant for ammonia production or the like, synthetic gas such as coal gasification gas, and exhaust gas from fossil fuel combustion, for example. In the cooling tower 30, the target gas is cooled to a predetermined temperature with cooling water from the cooler 32 in the packed section 31 and is then introduced to a lower part of the absorption tower 10 via the line $L_1$ by the blower $B_1$. The target gas may be cooled to 30 to 40° C., for example, from the viewpoint of the absorption efficiency in the absorption tower 10. The cooling water collected in the bottom of the cooling tower 30 is cooled by the cooler 32 via the line $L_2$ with the pump $P_2$ and is then supplied to the cooling tower 30 for cyclic use.

Subsequently, the target gas introduced from the line $L_1$ is brought into countercurrent contact with the amine-based absorbing solution introduced from the line $L_8$ in the lower packed section 11a and allows the amine-based absorbing solution to absorb $CO_2$ in the target gas for removal of $CO_2$ from the target gas. This process can remove 90% or more of $CO_2$ from the target gas. The amine-based absorbing solution is an aqueous solution of an amine compound. Examples of the amine compound are alkanolamines such as monoethanolamine, diethanolamine, diisopropanolamine, methyldiethanolamine, and triethanolamine.

The target gas having $CO_2$ removed is accompanied by the amine compound and water vaporized under high temperature due to exothermic reaction of $CO_2$ absorption. The target gas is accordingly brought into contact with the cleaning solution in the upper packed section 11b, where the water and amine compound in the gas are condensed and recovered into the cleaning solution. The target gas after washing is discharged from the top of the absorption tower 10 via the line $L_3$. The cleaning solution containing the water and amine compound is collected in the water receiver 11c. Some of the collected cleaning solution is cooled by the cooler 13 via the line $L_5$ with the pump $P_5$ and is then supplied to above the upper packed section 11b of the absorption tower 10 for cyclic use as the cleaning solution. A surplus of the collected cleaning solution is added to the line $L_8$ for the lean solution via the line $L_{5b}$ for cyclic use as the amine-based absorbing solution.

The rich solution having absorbed $CO_2$ is collected in the bottom of the absorption tower 10. Some of the collected rich solution is heated by the heat exchanger 25 via the line $L_4$ and is supplied to the regeneration tower 20. Some of the amine-based absorbing solution of the line $L_4$ is fed to the measurement apparatus 40 via the line $L_{4a}$ at predetermined intervals for measurement of the conductivity and viscosity. The measured values of the conductivity and viscosity are transmitted to the controller 50.

The rich solution supplied to the regeneration tower 20 releases $CO_2$ due to endothermic reaction in the lower packed section 21a as flowing down to be collected in the absorbing solution receiver 21c. The collected rich solution is supplied to the reboiler 22 via the line $L_7$ and is subjected to heat exchange with hot saturated steam from the line $L_6$ to be heated and release $CO_2$ contained in the rich solution. The saturated steam introduced to the reboiler 22 is condensed due to the heat exchange with the amine-based absorbing solution into saturated water, which is then discharged from the reboiler 22. The lean solution having released $CO_2$ is collected in the bottom of the regeneration tower 20.

The $CO_2$ gas separated from the amine-based absorbing solution is brought into gas-liquid contact with reflux water supplied from the line $L_9$ in the upper packed section 21b of the regeneration tower 20 for removal of the accompanied amine-based absorbing solution. The resultant gas is discharged from the top of the regeneration tower 20 via the line $L_{10}$. The $CO_2$ gas is cooled by the cooler 23, condensing the accompanied water vapor. The resultant is separated into $CO_2$ gas and condensed water in the gas-liquid separator 24. The separated $CO_2$ gas is discharged via the line $L_{11}$ to be recovered as pure $CO_2$ gas. The condensed water is supplied to the regeneration tower 20 via the line $L_9$ with the pump $P_9$ to be reused as the reflux water.

The lean solution collected in the bottom of the regeneration tower 20 is introduced into the heat exchanger 25 via the line $L_8$ and is then subjected to heat exchange with the rich solution to be cooled. The resultant lean solution is further cooled with the cooler 12 and is supplied to the absorption tower 10 for cyclic use as the amine-based absorbing solution. Some of the amine-based absorbing solution of the line $L_8$ is fed to the measurement apparatus 40 via the line $L_{8a}$ at predetermined intervals for measurement of the conductivity and viscosity. The measured values of the conductivity and viscosity are transmitted to the controller 50. The temperature of the amine-based absorbing solution to be supplied to the absorption tower 10 is adjusted by the heat exchanger 25 and cooler 12. In such a manner, the amine-based absorbing solution absorbs $CO_2$ in the absorption tower 10, releases $CO_2$ in the regeneration tower 20, and then absorbs $CO_2$ in the absorption tower 10 again for cyclic use.

The controller 50 calculates the $CO_2$ concentration of the amine-based absorbing solution from the measured values of the conductivity and viscosity obtained by the measurement apparatus 40 based on the aforementioned predetermined correlation. Based on the calculated value of the $CO_2$ concentration of the amine-based absorbing solution, the controller 50 then transmits a signal to the absorption tower 10, the reboiler 22 of the regeneration tower 20, and the like in order to change the operation conditions of the $CO_2$ recovery system.

In one or more embodiments of the present invention, the measurement apparatus 40 is capable of measuring the viscosity of the amine-based absorbing solution and the ultrasonic propagation velocity or conductivity thereof. The controller 50 is configured to calculate the $CO_2$ concentration and amine concentration of the amine-based absorbing solution from the measured value of the viscosity and the measured value of the ultrasonic propagation velocity or conductivity based on the correlation of the viscosity and the ultrasonic propagation velocity or conductivity with the $CO_2$ and amine concentrations in the amine-based absorbing solution. The measurement apparatus 40 may include a publicly-known viscometer and a publicly-known ultrasonic propagation velocity meter or conductivity meter.

According to one or more embodiments of the present invention, the measurement apparatus 40 measures the viscosity of the amine-based absorbing solution and the ultrasonic propagation velocity or conductivity thereof and transmits the results of measurement to the controller 50. The controller 50 calculates the $CO_2$ concentration and amine concentration of the amine-based absorbing solution from the measured value of the viscosity and the measured value of the ultrasonic propagation velocity or conductivity, which are transmitted from the measurement apparatus 40, based on the correlation of the viscosity and the ultrasonic propagation velocity or conductivity with the $CO_2$ and amine concentrations in the amine-based absorbing solution. Based on the calculated values of the $CO_2$ and amine concentrations of the amine-based absorbing solution, the controller 50 transmits a signal to the absorption tower 10, the reboiler 22 of the regeneration tower 20, and the like in order to change the operation conditions of the $CO_2$ recovery system.

In one or more embodiments of the present invention, the measurement apparatus 40 may also measure the viscosity and the ultrasonic propagation velocity or conductivity of the cleaning solution from the line $L_{5a}$ and the reflux water from the line $L_{9a}$. In this case, the controller 50 calculates the amine concentrations of the cleaning water and reflux water from the measured values transmitted from the measurement apparatus 40, based on the correlation among the viscosities of the cleaning water and reflux water, instead of the amine-based absorbing solution, the ultrasonic propagation velocities or conductivities thereof, and the amine concentrations. Based on the calculated values, the controller 50 transmits a signal in order to change the operation conditions of the absorption tower 10 and regeneration tower 20.

In one or more embodiments of the present invention, the measurement apparatus 40 may be capable of measuring the viscosity, ultrasonic propagation velocity, and conductivity of the amine-based absorbing solution. The controller 50 is configured to calculate the $CO_2$ concentration and amine concentration of the amine-based absorbing solution from the three measured values of the ultrasonic propagation velocity, viscosity, and conductivity based on the correlation of the value of the ultrasonic propagation velocity of the amine-based absorbing solution corrected using the viscosity and the conductivity or the value of the conductivity corrected using the viscosity with the $CO_2$ and amine concentrations.

The measurement apparatus 40 may include a publicly-known viscometer, ultrasonic propagation velocity meter, and conductivity meter. As the aforementioned correlation, the controller 50 can use the correlation with the conductivity and the product of the ultrasonic propagation velocity and an exponential function with a base of the viscosity (for example, the viscosity raised to the power of $-\frac{1}{2}$ or $\frac{1}{2}$) and the correlation with the product of the conductivity and the viscosity and the product of the ultrasonic propagation velocity and an exponential function with a base of the viscosity (for example, the viscosity raised to the power of $-\frac{1}{2}$ or $\frac{1}{2}$), for example.

According to one or more embodiments of the present invention, the measurement apparatus 40 measures three physical properties including viscosity, ultrasonic propagation velocity, and conductivity of the amine-based absorbing solution and transmits the results of measurement to the controller 50. The controller 50 calculates the $CO_2$ and amine concentrations of the amine-based absorbing solution from the three measured values transmitted from the measurement apparatus 40 based on the correlation of the value of the ultrasonic propagation velocity corrected using the viscosity and the conductivity or the value of the conductivity corrected using the viscosity with the $CO_2$ and amine concentrations in the amine-based absorbing solution. Based on the calculated values, the controller 50 transmits a signal to the absorption tower 10, the reboiler 22 of the regeneration tower 20, or the like in order to change the operation conditions of the $CO_2$ recovery system.

In one or more embodiments of the present invention, the measurement apparatus 40 is further capable of measuring the temperature of the amine-based absorbing solution. The controller 50 corrects the aforementioned correlation according to the measured value of the temperature of the amine-based absorbing solution and calculates the $CO_2$ concentration of the amine-based absorbing solution and the like from the aforementioned measured values of the viscosity and the like. The conductivity, viscosity, and ultrasonic propagation velocity of the amine-based absorbing solution are temperature-dependent and take different values depending on the measured temperature even if the amine-based absorbing solution has the same composition. In one or more embodiments of the present invention, the aforementioned correlation is corrected by measuring the temperature. This allows for accurate calculation of the $CO_2$ and amine concentrations of the amine-based absorbing solution even if the temperature of the amine-based absorbing solution varies greatly.

The measurement apparatus 40 of one or more embodiments of the present invention may include a publicly-known thermometer in addition to the aforementioned meters. In terms of at least one of the viscosity, conductivity, and ultrasonic propagation velocity of the amine-based absorbing solution, the controller 50 as described herein is configured to store data of a correlation (temperature correlation) in the amine-based absorbing solution between each of the aforementioned properties and the temperature when the $CO_2$ and amine concentrations of the amine-based absorbing solution are constant. In one or more embodiments, the range of temperature in the temperature correlation is preferably 10 to 130° C. and more preferably 20 to 50° C., for example. The preferred ranges of the $CO_2$ and amine concentrations of the amine-based absorbing solution are the same as described above.

The controller 50 of one or more embodiments of the present invention is configured to also store a correlation (referred to as $CO_2$ concentration correlation) for calculating the $CO_2$ concentration as described above. Specifically, the $CO_2$ concentration correlation is: the correlation between the value of the conductivity corrected using the viscosity and the $CO_2$ concentration of the amine-based absorbing solution; the correlation among the viscosity of the amine-based absorbing solution, the conductivity or ultrasonic propagation velocity, and the $CO_2$ concentration; the correlation among the value of the ultrasonic propagation velocity corrected using the viscosity, the conductivity or the value of the conductivity corrected using the viscosity, and the $CO_2$ concentration. The temperature (referred to as reference temperature) at which the $CO_2$ concentration correlation is established is not particularly limited within the temperature range of the aforementioned temperature correlation and is 20° C., for example. The controller 50 of one or more embodiments of the present invention includes a function to correct the aforementioned $CO_2$ concentration correlation using the temperature correlation into a correlation that can be established at the measured temperature.

According to one or more embodiments of the present invention, the measurement apparatus 40 measures the viscosity of the amine-based absorbing solution, at least one of the ultrasonic propagation velocity and conductivity of the amine-based absorbing solution, and the temperature of the amine-based absorbing solution and transmits the measurement results to the controller 50. The controller 50, using the temperature correlation based on the measured value of the temperature of the amine-based absorbing solution, interpolates the $CO_2$ concentration correlation to create a correlation that can be established at the measured temperature (for example, the values of the viscosity, conductivity, and ultrasonic propagation velocity in the correlation established at the reference temperature are corrected to values at the measured temperature using the temperature correlation, and using the corrected values of the viscosity, conductivity, and ultrasonic propagation velocity, the correlation relationship with the $CO_2$ concentration is replotted). Based on the temperature-corrected $CO_2$ concentration correlation, the controller 50 calculates the $CO_2$ concentration of the amine-based absorbing solution or the $CO_2$ and amine concentrations thereof from the measured values of the viscosity, conductivity, and ultrasonic propagation velocity of the amine-based absorbing solution transmitted from the measurement apparatus 40. Based on the calculated values, the controller 50 transmits a signal to the absorption tower 10, the reboiler 22 of the regeneration tower 20, or the like in order to change the operation conditions of the $CO_2$ recovery system.

As described above, in one or more embodiments of the present invention, the viscosity, conductivity, ultrasonic propagation velocity, and temperature, if necessary, of the amine-based absorbing solution which can be automatically measured online, are measured by the measurement apparatus 40. The $CO_2$ concentration of the amine-based absorbing solution can be calculated quickly with high accuracy with the controller 50 regardless of whether the amine concentration of the amine-based absorbing solution is high or low since the value of the conductivity corrected using the viscosity correlates with the $CO_2$ concentration of the amine-based absorbing solution; the viscosity of the amine-based absorbing solution, and the conductivity or ultrasonic propagation velocity of the amine-based absorbing solution, the $CO_2$ concentration correlate with each other; or the value of the ultrasonic propagation velocity of the amine-based absorbing solution corrected using the viscosity, the conductivity or the value of the conductivity corrected using the viscosity, and the $CO_2$ concentration correlate with each other.

EXAMPLES

Hereinafter, a description is given of Examples and Comparative Examples of one or more embodiments of the present invention.

Example 1

Each of four types of amine-based absorbing solutions of different amine concentration compound was caused to absorb four different amounts of $CO_2$, preparing 16 amine-based absorbing solutions having different combinations of $CO_2$ concentration and amine concentration. These amine-based absorbing solutions were measured in terms of conductivity, viscosity, and $CO_2$ concentration. The results are plotted in FIG. 2 so as to show the relationship of the $CO_2$ concentration to the conductivity (Comparative Example) and are plotted in FIG. 3 so as to show the relationship of the $CO_2$ concentration to the product of the conductivity and viscosity (Example). The amine concentration was adjusted in a range from 40 to 60 wt %. The amine concentration A % was the lowest, followed in ascending order by B %, C %, and D %.

As for the $CO_2$ concentration (wt %), inorganic carbon was measured using a total organic carbon meter provided with an NDIR detector. The amine concentration (wt %) was measured by ion chromatography including a conductivity detector. The conductivity (mS/cm) and viscosity (Pa·s), which are temperature-dependent, were measured at the same temperature (20° C.).

Figure 2:
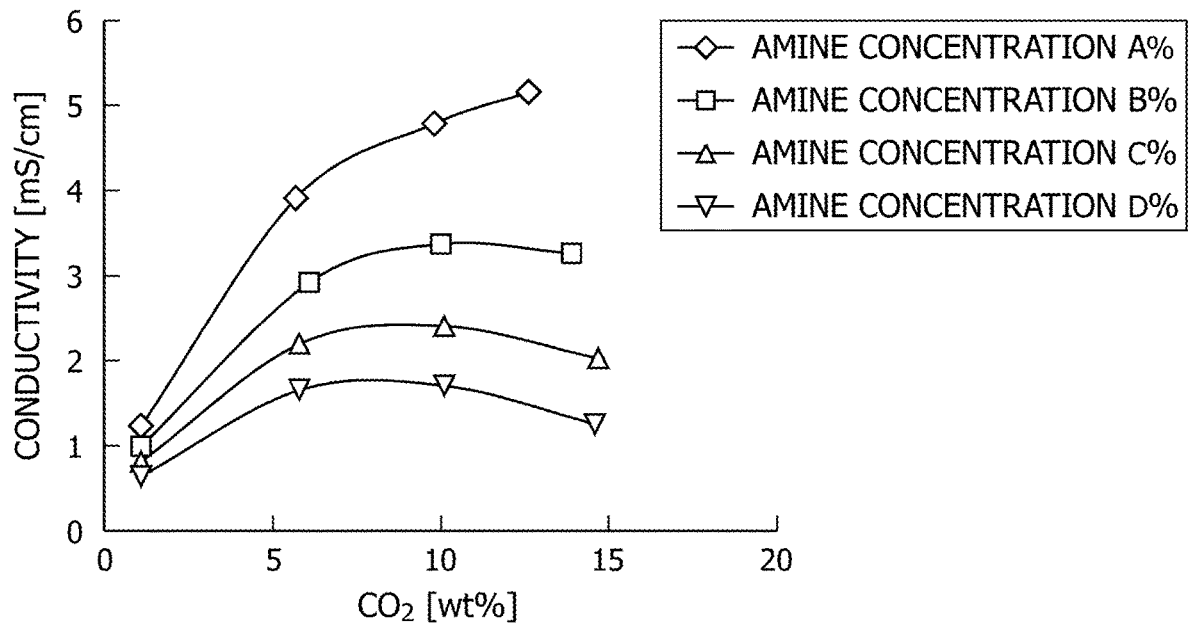
FIG. 2 is a graph showing the relationship between conductivity and $CO_2$ concentration for absorbing solutions of different amine concentrations (Comparative Example).

In the graph shown in FIG. 2, when the $CO_2$ concentration of the amine-based absorbing solution increased from about 1 wt % to about 5 wt %, the conductivity also increased. The value of the $CO_2$ concentration in this range can be specified from a measured value of the conductivity when the amine concentration of the amine-based absorbing solution is known. However, when the $CO_2$ concentration further increases to about 10 wt %, the conductivity of the amine-based absorbing solutions having an amine concentration of B, C, and D % does not increase so much. When the $CO_2$ concentration increases and exceeds about 15 wt %, the conductivity thereof decreases. It is therefore difficult to calculate the $CO_2$ concentration from only the measured value of the conductivity even if the amine concentration of the amine-based absorbing solution is known.

Figure 3:
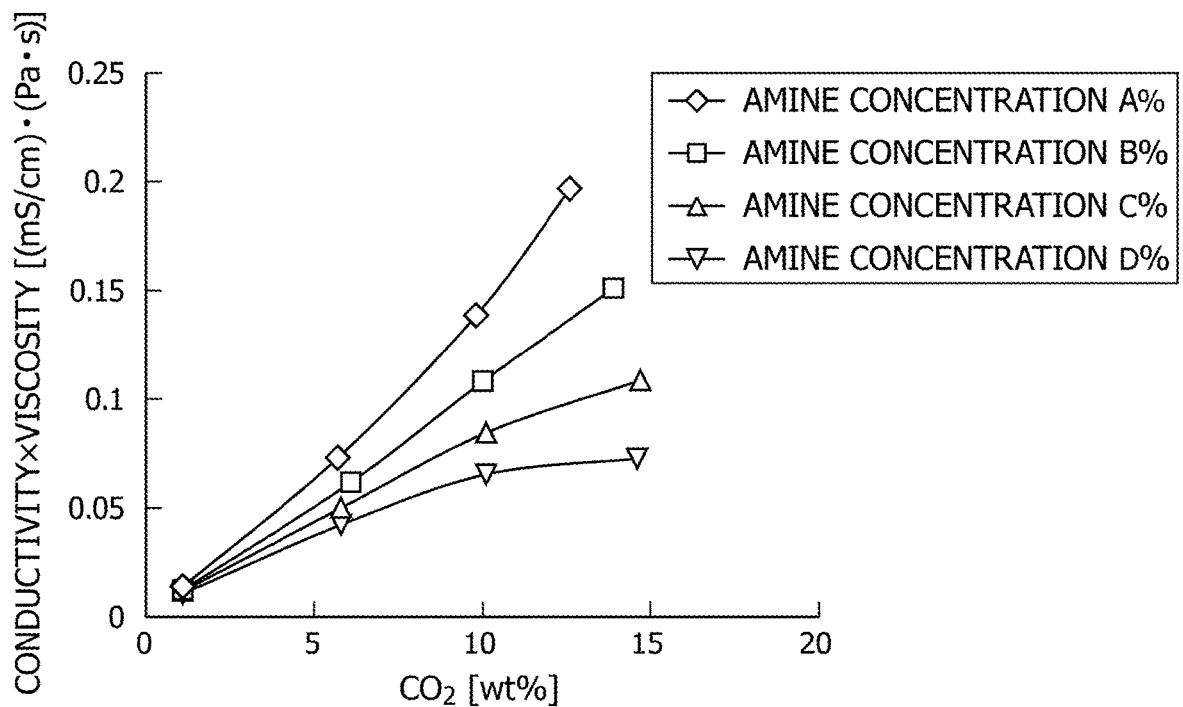
FIG. 3 is a graph showing the relationship between the product of the conductivity and viscosity and the $CO_2$ concentration for absorbing solutions of different amine concentration (Example).

In the graph shown in FIG. 3, the $CO_2$ concentration increases with the product of the conductivity and viscosity for the amine-based absorbing solutions of any amine concentration, showing high correlation between the $CO_2$ concentration and the product of the conductivity and viscosity. This reveals that the $CO_2$ concentration of the amine-based absorbing solution can be calculated by multiplying the measured value of the conductivity by the measured value of the viscosity. Generally, the larger the amount of electrolyte dissolved in a solvent, the higher the conductivity. However, such a rule is not directly applicable to $CO_2$ dissolved in the amine-based absorbing solution. The reason that the correction of the conductivity using the viscosity results in the high correlation mentioned above as shown in FIG. 3 is thought to be as follows. In the region where the amount of dissolved $CO_2$ is low, dissolution of $CO_2$ does not increase the viscosity of the amine-based absorbing solution so much, and the viscosity therefore cannot affect the measured value of the conductivity. In the region where the amount of dissolved $CO_2$ is high, the viscosity of the amine-based absorbing solution significantly increases with the amount of dissolved $CO_2$, preventing the electrolyte from moving and reducing the measured value of the conductivity.

Example 2

The 16 amine-based absorbing solutions used in Example 1 were measured in terms of the ultrasonic propagation velocity (sonic velocity) in addition to the conductivity, viscosity, and $CO_2$ concentration. The sonic velocity (m/s) is temperature-dependent and is measured at the same temperature as that at the process of measuring the conductivity and viscosity. The results are plotted in FIG. 4 so as to show the relationship of the sonic velocity to the conductivity (Comparative Example); are plotted in FIG. 5 so as to show the relationship of the sonic velocity to the viscosity (Example); and are plotted in FIG. 6 so as to show the relationship of the viscosity to the conductivity (Example). The values of the $CO_2$ concentration in the legend of each graph are representative values. The accurate values of the $CO_2$ concentration are shown in the graphs of FIGS. 2 and 3.

Figure 4:
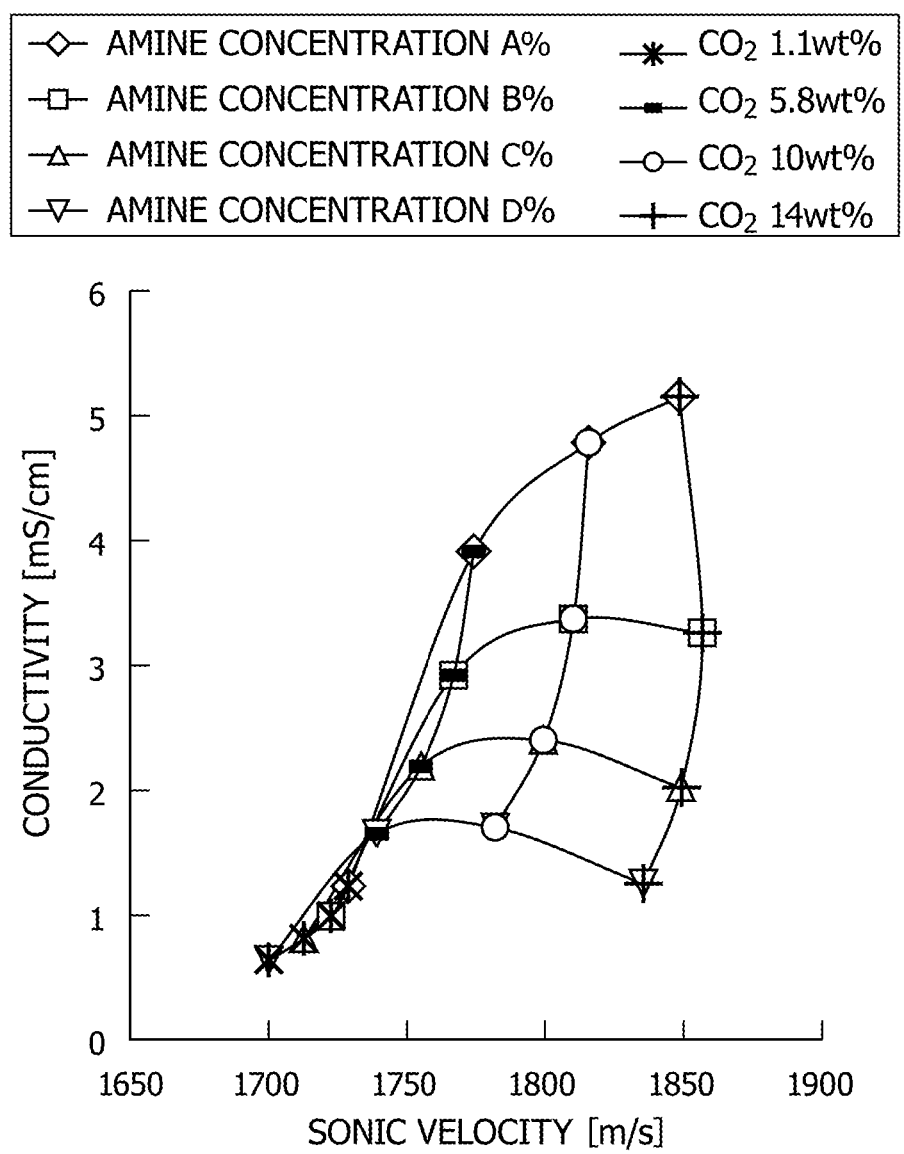
FIG. 4 is a graph showing the relationship between the conductivity and the sonic velocity for the absorbing solutions of different combinations of amine concentration and $CO_2$ concentration (Comparative Example).

In the graph shown in FIG. 4, when the $CO_2$ concentration of the absorbent amino solution is about 10 wt % and about 14 wt %, the amine concentration and $CO_2$ concentration were individually specified from two measured values of the conductivity and sonic velocity. When the $CO_2$ concentration is 1.1 wt % and 5.8 wt %, the plotted curves are kinked near the sonic velocity of 1740 m/s and the conductivity of 1.65 mS/cm. It is therefore difficult to uniquely specify the amine concentration and $CO_2$ concentration from two measured values of the conductivity and sonic velocity.

Figure 5:
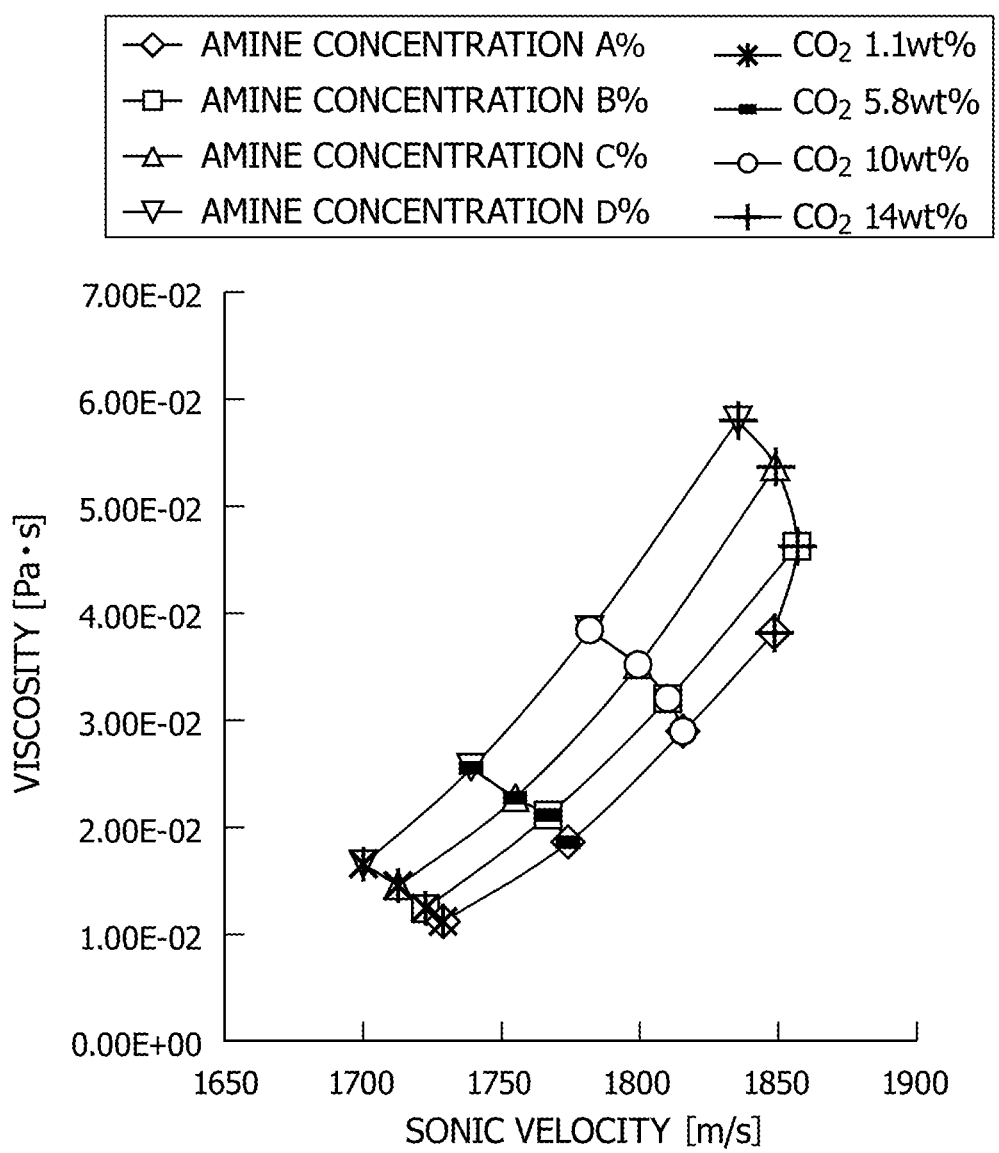
FIG. 5 is a graph showing the relationship between the viscosity and the sonic velocity for the absorbing solutions of different combinations of amine concentration and $CO_2$ concentration (Example).
Figure 6:
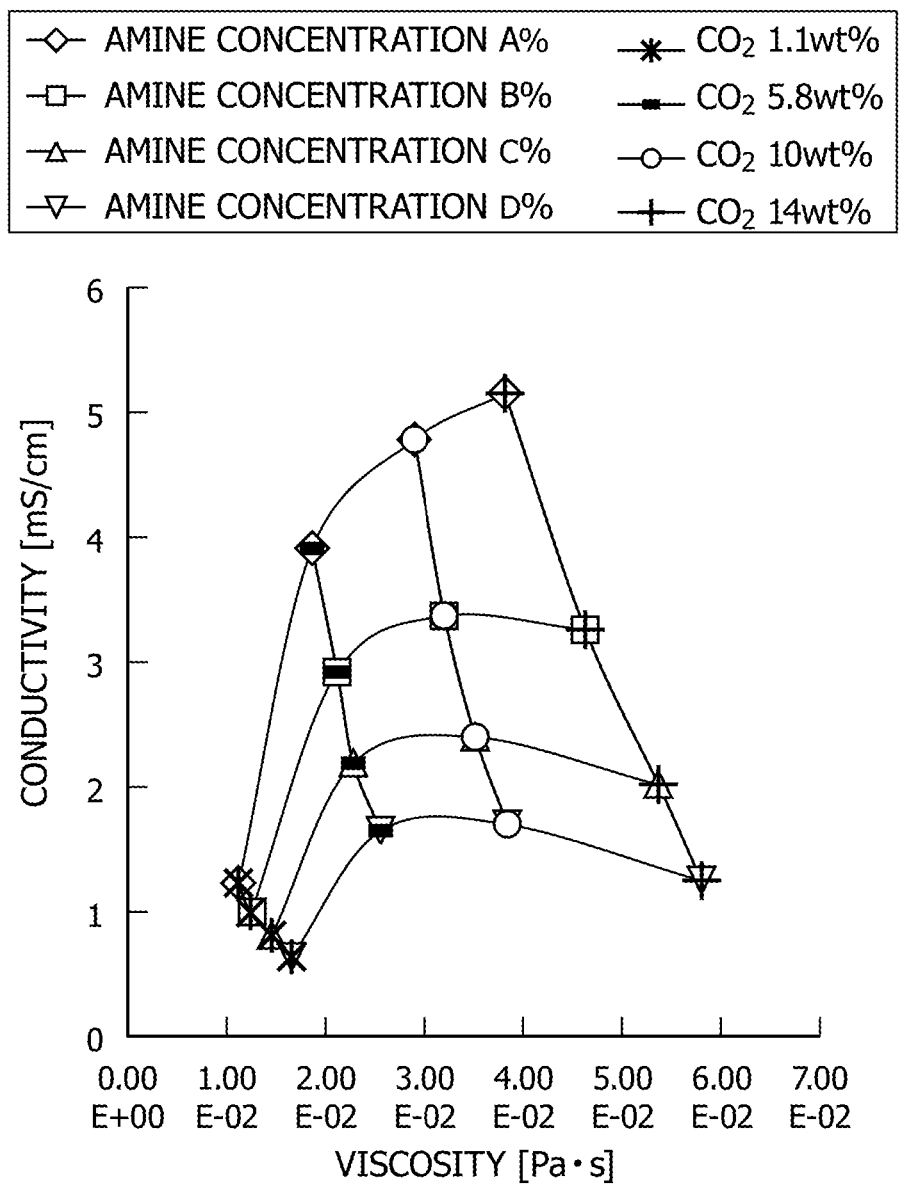
FIG. 6 is a graph showing the relationship between the conductivity and the viscosity for the absorbing solutions of different combinations of amine concentration and $CO_2$ concentration (Example).

In the graph shown in FIG. 5, the plotted curves are not kinked. The amine concentration and $CO_2$ concentration were individually uniquely specified from two measured values of the conductivity and sonic velocity. In the graph shown in FIG. 6, the plotted curves are not kinked. The amine concentration and $CO_2$ concentration were individually uniquely specified from two the measured values of the conductivity and viscosity.

Example 3

Figure 7:
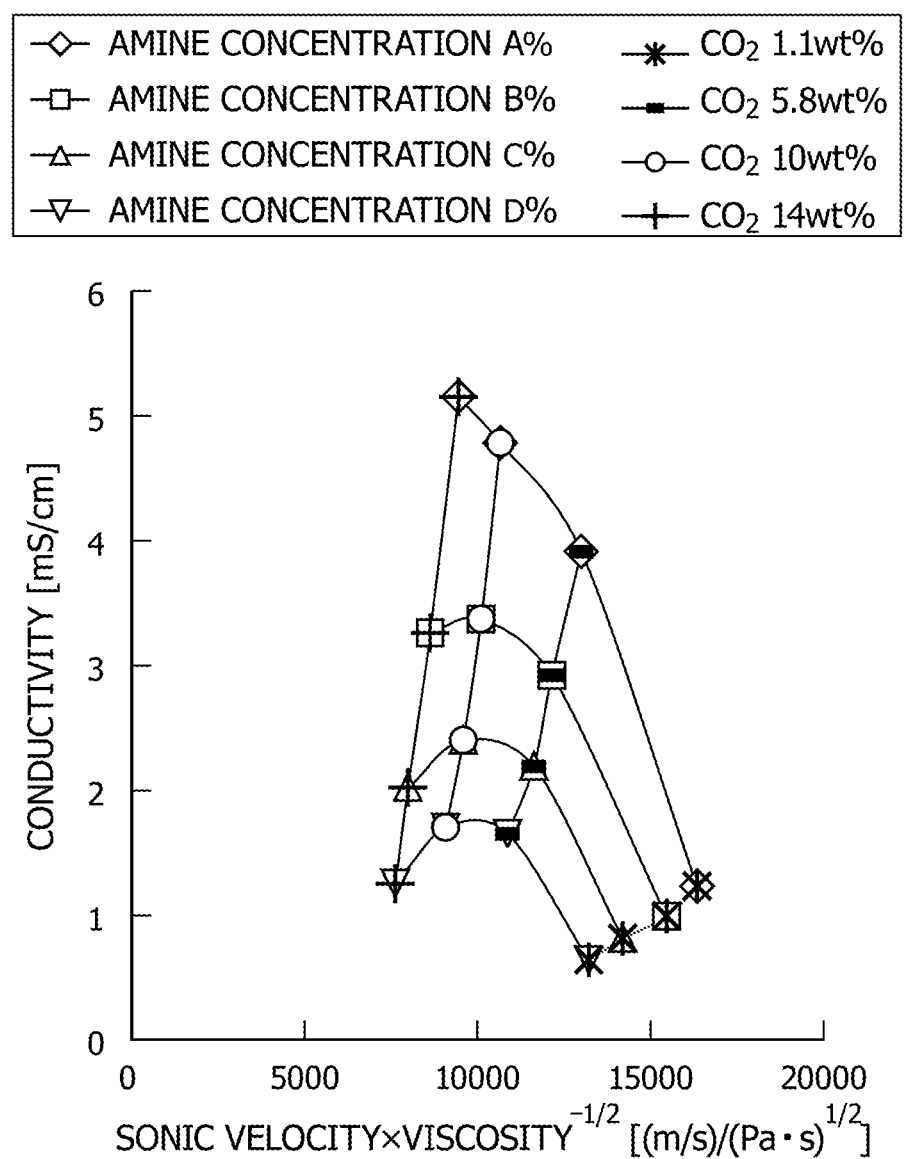
FIG. 7 is a graph showing the relationship between the conductivity and the product of the sonic velocity and viscosity to the power of $-\frac{1}{2}$ for the absorbing solutions of different combinations of amine concentration and $CO_2$ concentration (Example).
Figure 8:
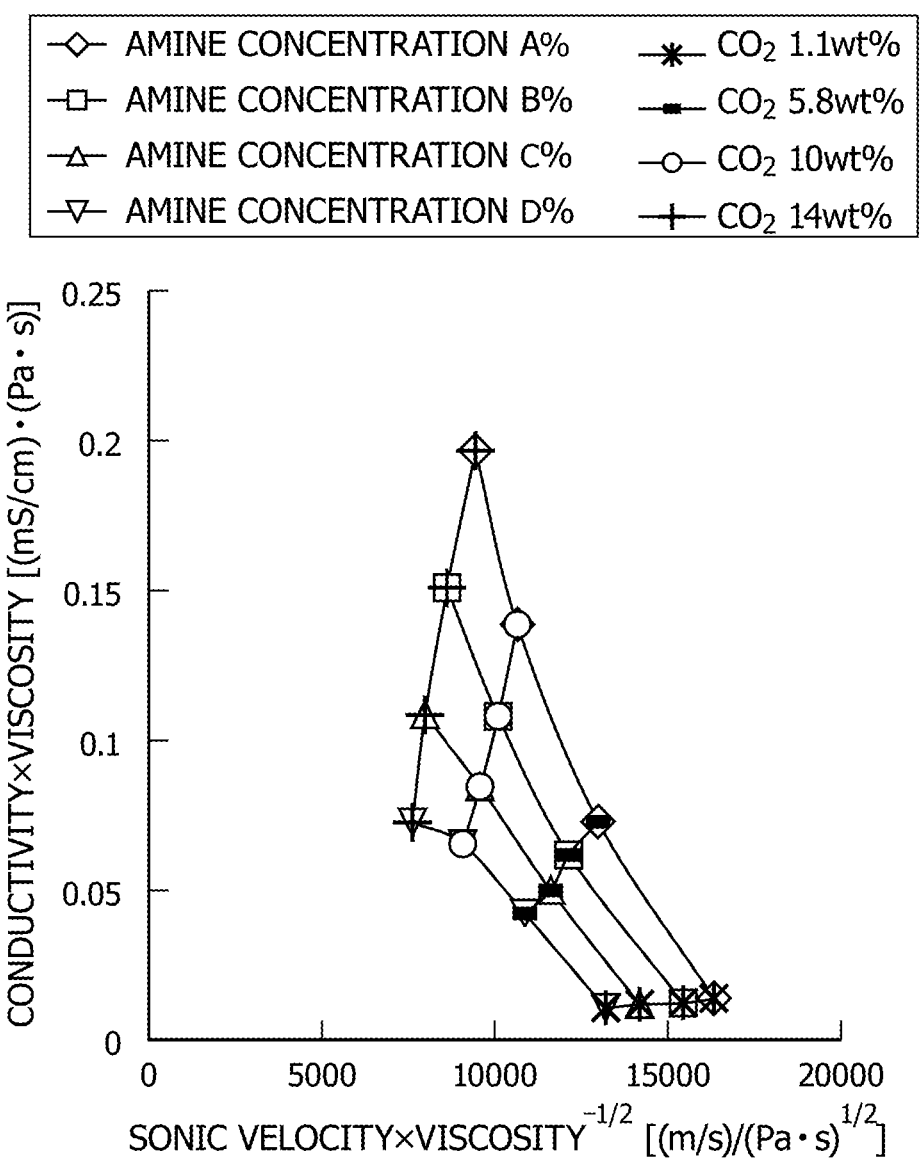
FIG. 8 is a graph showing the relationship between the product of the conductivity and viscosity and the product of the sonic velocity and viscosity to the power of $-\frac{1}{2}$ for the absorbing solutions different combinations of amine concentration and $CO_2$ concentration (Example).

The results of measuring the conductivity, viscosity, $CO_2$ concentration, and ultrasonic propagation velocity (sonic velocity) of the 16 amine-based absorbing solutions used in Example 2 are plotted in FIG. 7 so as to show the relationship of the product of the sonic velocity and the velocity raised to the power of $-\frac{1}{2}$, to the conductivity (Example) and are plotted in FIG. 8 so as to show the relationship of the product of the sonic velocity and the velocity raised to the power of $-\frac{1}{2}$ to the product of the conductivity and viscosity (Example).

The horizontal axis in the graph shown in FIG. 7 shows the product of the sonic velocity and the viscosity to the power of $-\frac{1}{2}$ instead of the sonic velocity in FIG. 4 showing Comparative Example described above. This eliminates the kink of the plotted curves and allows the amine concentration and $CO_2$ concentration to be individually specified uniquely from three measured values of the conductivity, viscosity, and sonic velocity. The sonic velocity exhibits a relationship (c: sonic velocity, k: bulk modulus, p: density) according to the following expression. Generally, liquid of higher viscosity has a greater bulk modulus. Dissolution of $CO_2$ and amine increases the density and viscosity of the amine-based absorbing solution. The sonic velocity decreases with the increase in density and increases with the increase in the viscosity (bulk modulus). Similarly to the conductivity, it is thought that the sonic velocity is affected by the viscosity in addition to the amounts of $CO_2$ and amine dissolved.

$$c=\sqrt{(K/\rho)} \qquad \text{[Equation 1]}$$

The vertical axis in the graph shown in FIG. 8 represents the product of the conductivity and viscosity instead of the conductivity shown in FIG. 7. The plotted curves corresponding to the amine-based absorbing solutions of the same amine concentration therefore bend very gently, so that the amine concentration and $CO_2$ concentration can be easily specified from three measured values of the conductivity, viscosity, and sonic velocity. This is thought to be because the relationship between the amount of dissolved $CO_2$ and the conductivity of the amine-based absorbing solution is corrected for the viscosity in a similar manner to Example 1.

Example 4

Figure 9:
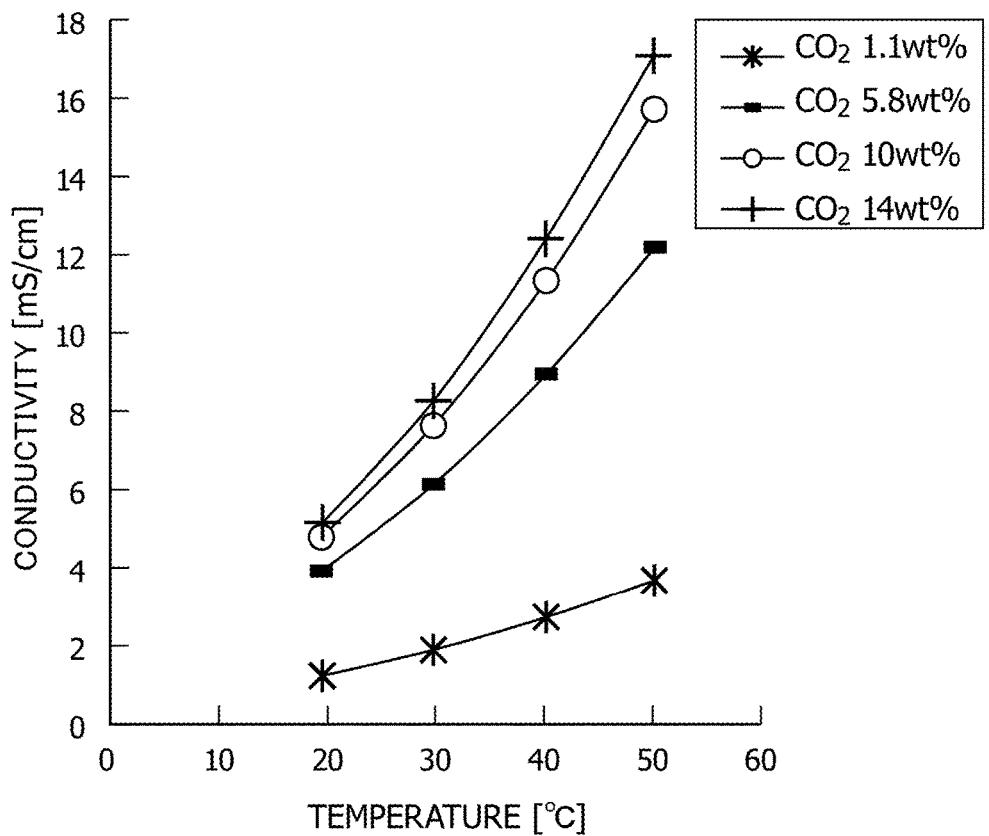
FIG. 9 is a graph showing the relationship between the conductivity and temperature for the absorbing solutions of different $CO_2$ concentrations according to one or more embodiments.
Figure 10:
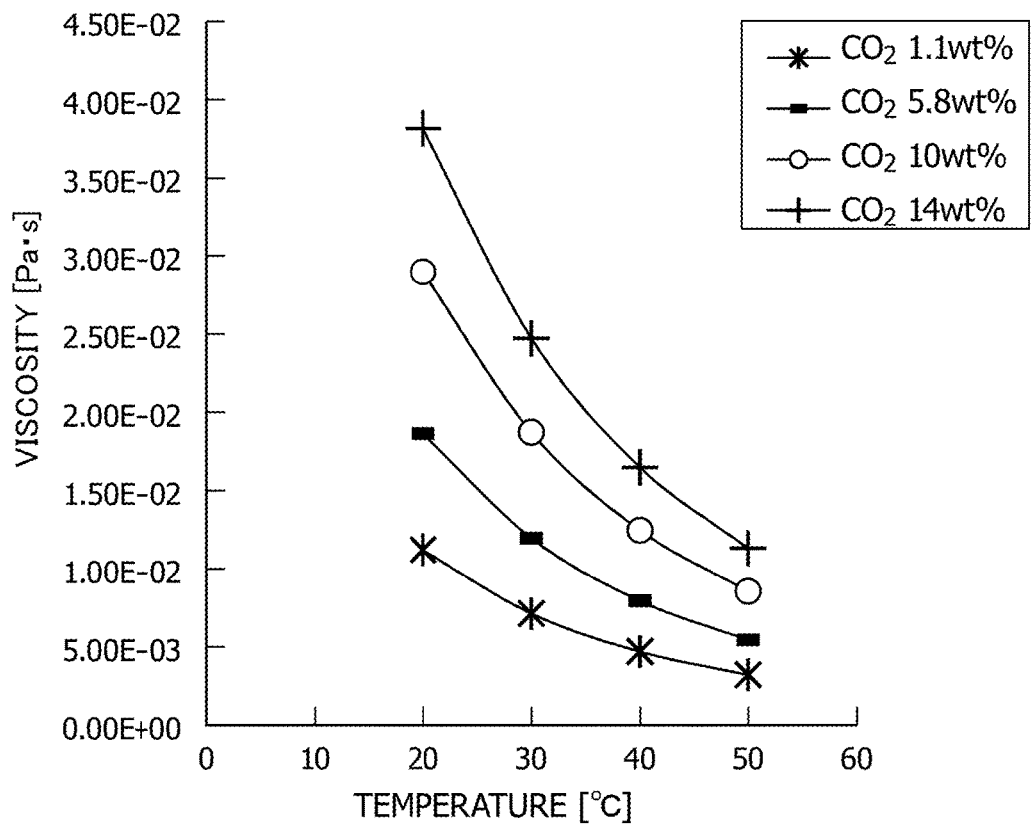
FIG. 10 is a graph showing the relationship between the viscosity and temperature for the absorbing solutions of different $CO_2$ concentration according to one or more embodiments.
Figure 11:
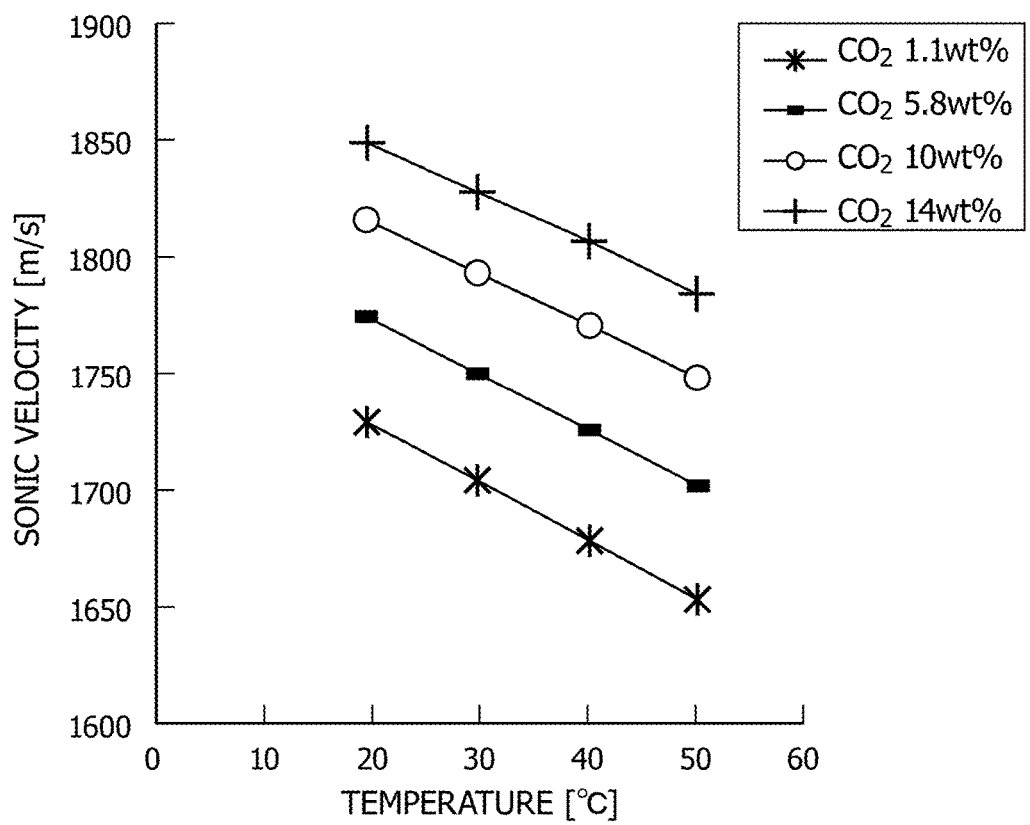
FIG. 11 is a graph showing the relationship between the sonic velocity and temperature for the absorbing solutions of different $CO_2$ concentration according to one or more embodiments.

The 16 types of amine-based absorbing solutions used in Example 1 were measured in terms of the conductivity, viscosity, and ultrasonic propagation velocity (sonic velocity) with the temperature raised from 20° C. to 50° C. stepwise by 10° C. FIGS. 9, 10, and 11 show the measurement results in the case where the amine concentration is A %. As shown in these diagrams, the result for either value of the $CO_2$ concentration shows a correlation in which the higher the temperature, the higher the measured value of the conductivity and the lower the measured values of the viscosity and sonic velocity. The results for the other amine concentrations show the same correlation (not shown).

Figure 12:
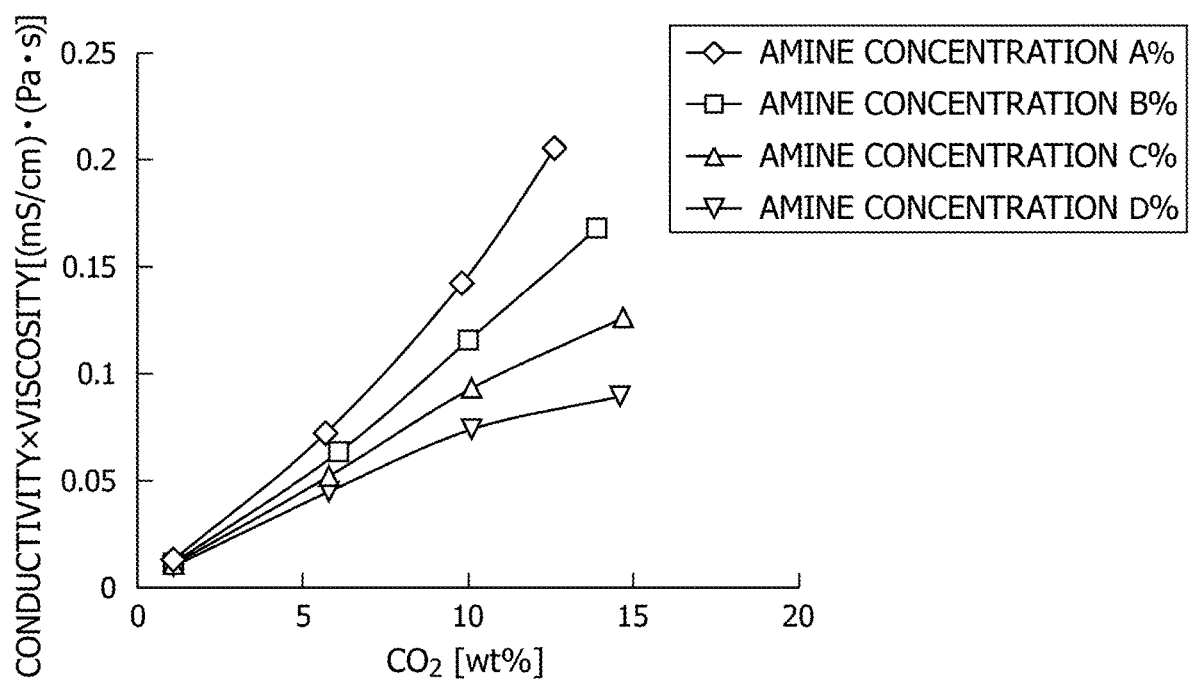
FIG. 12 is a graph showing the relationship between the product of temperature-corrected conductivity and viscosity and the $CO_2$ concentration for the absorbing solutions of different $CO_2$ concentration according to one or more embodiments.

Based on the data of the temperature correlation, the correlation between the $CO_2$ concentration and the product of the conductivity and viscosity in Example 1 shown in FIG. 3, where the amine-based absorbing solution is 20° C., is corrected to a correlation for the amine-based absorbing solution at 35° C. The graph of the corrected correlation is shown in FIG. 12. FIG. 12 is obtained by correcting the values of the conductivity and viscosity in FIG. 3 to the values at 35° C. using the temperature correlations shown in FIGS. 9 and 10, calculating the product of the corrected conductivity and viscosity, and replotting the relationship between the calculated product and the $CO_2$ concentration. The $CO_2$ concentration and amine concentration of the amine-based absorbing solution were actually measured at 35° C. The measurement results thereof were the same as those at 20° C. This reveals that the correlation between the $CO_2$ concentration and the product of the temperature-correlated conductivity and viscosity in FIG. 12 was really established.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SYMBOL LIST

10 Absorption tower
11*a* Lower packed section
11*b* Upper packed section
11*c* Water receiver
12, 13, 23, 32 Cooler
20 Regeneration tower
22 Reboiler
24 Gas-liquid separator
25 Heat exchanger
30 Cooling tower
31 Packed section
40 Iron ion analyzer
50 Reclaiming apparatus

The invention claimed is:

1. A system for analyzing a $CO_2$ concentration of an amine-based absorbing solution, the system comprising:
   a measurement apparatus that measures a viscosity of the amine-based absorbing solution and at least one selected from conductivity and ultrasonic propagation velocity of the amine-based absorbing solution, wherein the amine-based absorbing solution absorbs and removes $CO_2$ from a target gas by gas-liquid contact with the target gas; and
   a controller that determines the $CO_2$ concentration of the amine-based absorbing solution from results measured by the measurement apparatus.

2. The system according to claim 1, wherein the controller determines the $CO_2$ concentration of the amine-based absorbing solution by correcting the measured conductivity of the amine-based absorbing solution using the measured viscosity thereof based on a correlation between a corrected value of the conductivity of the amine-based absorbing solution using the viscosity thereof and the $CO_2$ concentration of the amine-based absorbing solution.

3. The system according to claim 1, wherein the controller determines the $CO_2$ concentration and an amine concentration of the amine-based absorbing solution from the measured viscosity and the measured conductivity or ultrasonic propagation velocity of the amine-based absorbing solution based on a correlation among viscosity of the amine-based absorbing solution, conductivity or ultrasonic propagation velocity of the amine-based absorbing solution, the $CO_2$ concentration and the amine concentration of the amine-based absorbing solution.

4. The system according to claim 1, wherein the controller determines the $CO_2$ concentration and an amine concentration of the amine-based absorbing solution from three measured values of the ultrasonic propagation velocity, viscosity, and conductivity of the amine-based absorbing solution based on a correlation among a corrected value of the ultrasonic propagation velocity of the amine-based absorbing solution using the viscosity, thereof, the conductivity, or a corrected value of the conductivity of the amine-based absorbing solution using the viscosity thereof, the $CO_2$ concentration and the amine concentration of the amine-based absorbing solution.

5. The system according to claim 1, wherein the measurement apparatus measures a temperature of the amine-based absorbing solution, and wherein the controller determines the $CO_2$ concentration of the amine-based absorbing solution or the $CO_2$ concentration and an amine concentration of the amine-based absorbing solution from a measured viscosity of the amine-based absorbing solution, at least one selected from the measured conductivity and the measured ultrasonic propagation velocity of the amine-based absorbing solution, and the measured temperature of the amine-based absorbing solution.

6. The system according to claim 1, wherein the measurement apparatus measures the viscosity and at least one selected from conductivity and ultrasonic propagation velocity of the amine-based absorbing solution at a certain temperature after the amine-based absorbing solution is adjusted to the certain temperature.

7. A $CO_2$ recovery system comprising:
   the system for analyzing a $CO_2$ concentration of an amine-based absorbing solution according to claim 1;
   a $CO_2$ absorption tower that removes the $CO_2$ from target gas by bringing the target gas containing the $CO_2$ into gas-liquid contact with the amine-based absorbing solution and causing the amine-based absorbing solution to absorb $CO_2$; and
   an absorbing solution regeneration tower that regenerates the amine-based absorbing solution by releasing the $CO_2$ from the amine-based absorbing solution that has absorbed $CO_2$ in the $CO_2$ absorption tower.

8. A method of operating the $CO_2$ recovery system according to claim 7, the method comprising:
   measuring the viscosity of the amine-based absorbing solution and at least one selected from conductivity and ultrasonic propagation velocity of the amine-based absorbing solution; and
   determining the $CO_2$ concentration of the amine-based absorbing solution from results comprising a measured viscosity and at least one selected from a measured conductivity and a measured ultrasonic propagation velocity of the amine-based absorbing solution.

* * * * *